(12) United States Patent
Heath

(10) Patent No.: US 7,228,184 B2
(45) Date of Patent: Jun. 5, 2007

(54) VIRAL-INHIBITING METHOD

(76) Inventor: Chester Heath, 490 E. Buckley Ave., Springville, UT (US) 84663

( * ) Notice: Subject to any disclaimer, the term of this patent is extended or adjusted under 35 U.S.C. 154(b) by 517 days.

(21) Appl. No.: 10/371,732

(22) Filed: Feb. 22, 2003

(65) Prior Publication Data

US 2004/0167589 A1 Aug. 26, 2004

(51) Int. Cl.
*A61N 1/18* (2006.01)
(52) U.S. Cl. .......................... 607/68; 607/2
(58) Field of Classification Search ............... 607/1–2, 607/50, 66, 67, 72, 115, 149, 150
See application file for complete search history.

(56) References Cited

U.S. PATENT DOCUMENTS

| | | | | |
|---|---|---|---|---|
| 3,924,641 A | * | 12/1975 | Weiss ........................... | 607/74 |
| 4,068,669 A | * | 1/1978 | Niemi .......................... | 607/63 |
| 4,381,010 A | * | 4/1983 | Thompson et al. ............ | 607/9 |
| 4,543,956 A | * | 10/1985 | Herscovici .................... | 607/13 |
| 4,821,723 A | * | 4/1989 | Baker et al. ................... | 607/7 |
| 4,913,148 A | * | 4/1990 | Diethelm ...................... | 607/72 |
| 4,924,880 A | * | 5/1990 | O'Neill et al. ................ | 607/47 |
| 4,977,895 A | * | 12/1990 | Tannenbaum ................. | 607/46 |
| 4,989,605 A | * | 2/1991 | Rossen ......................... | 607/46 |
| 5,133,352 A | | 7/1992 | Lathrop et al. ......... | 128/419 R |
| 5,470,349 A | * | 11/1995 | Kleditsch et al. ............. | 607/75 |
| 5,607,461 A | | 3/1997 | Lathrop ........................ | 607/75 |
| 5,674,261 A | * | 10/1997 | Smith ........................... | 607/46 |
| 5,871,506 A | * | 2/1999 | Mower .......................... | 607/9 |
| 6,083,250 A | | 7/2000 | Lathrop ........................ | 607/50 |
| 6,594,527 B2 | * | 7/2003 | Mo .............................. | 607/74 |
| 6,618,625 B2 | * | 9/2003 | Silverstone ................... | 607/72 |
| 2002/0099426 A1 | | 7/2002 | Silverstone | |

* cited by examiner

*Primary Examiner*—Kristen Mullen
(74) *Attorney, Agent, or Firm*—Lynn G. Foster

(57) ABSTRACT

A hand-held viral inhibitor and related methodology which transfer between space exposed electrodes an electric current signal of reversing polarity through the viral-laden tissue are disclosed.

11 Claims, 3 Drawing Sheets

US 7,228,184 B2

VIRAL-INHIBITING METHOD

FIELD OF THE INVENTION

The present invention relates generally to curtailing viral phenomenon and, more particularly, to viral-inhibiting apparatus and methods, which impose an electric current signal of reversing polarity upon the viral laden region.

BACKGROUND

The presence of a virus in the body manifests itself various as fever blisters, genital affliction, lesions, warts, growths, etc., with the attending pain, burning, irritation, swelling, itching, and embarrassment.

Because viral infections are often long term and repetitive, providing technology to inhibit the same, immediately and continuously available to the afflicted person, would be a valuable benefit to the individuals specifically and to mankind generally.

BRIEF SUMMARY AND OBJECTS OF THE PRESENT INVENTION

In brief summary the present invention overcomes or substantially alleviates problems of the past pertaining to inhibiting viral phenomenon, by apparatus and methodology which impose an electric current signal of reversing polarity upon the viral-laden site.

With the foregoing in mind, it is a primary object to overcome or substantially alleviate problems of the past in inhibiting viral phenomenon.

Another paramount object is to inhibit viral phenomenon using apparatus and methodology which impose an electric current signal between electrodes first in one direction and then in another direction.

A further significant object is the provision of novel apparatus and methodology for inhibiting viral phenomenon, which are immediately and continuously available to the person afflicted.

Another important object is the provision of viral inhibiting apparatus having one or more of the following features: hand-held; self operable; reduces severity and frequency of the ailment; non-invasive; cost effective; low maintenance; long lasting although discardable and replaceable when and if contaminated; essentially painless; low power; conserves power; applicable to various wave forms; provides for rapid transition between polarity reversals; and solves a long existing unsatisfied need.

These and other objects and features of the present invention will be apparent from the detailed description taken with reference to accompanying drawings.

DETAILED DESCRIPTION OF THE ILLUSTRATED EMBODIMENTS

Figure 1:
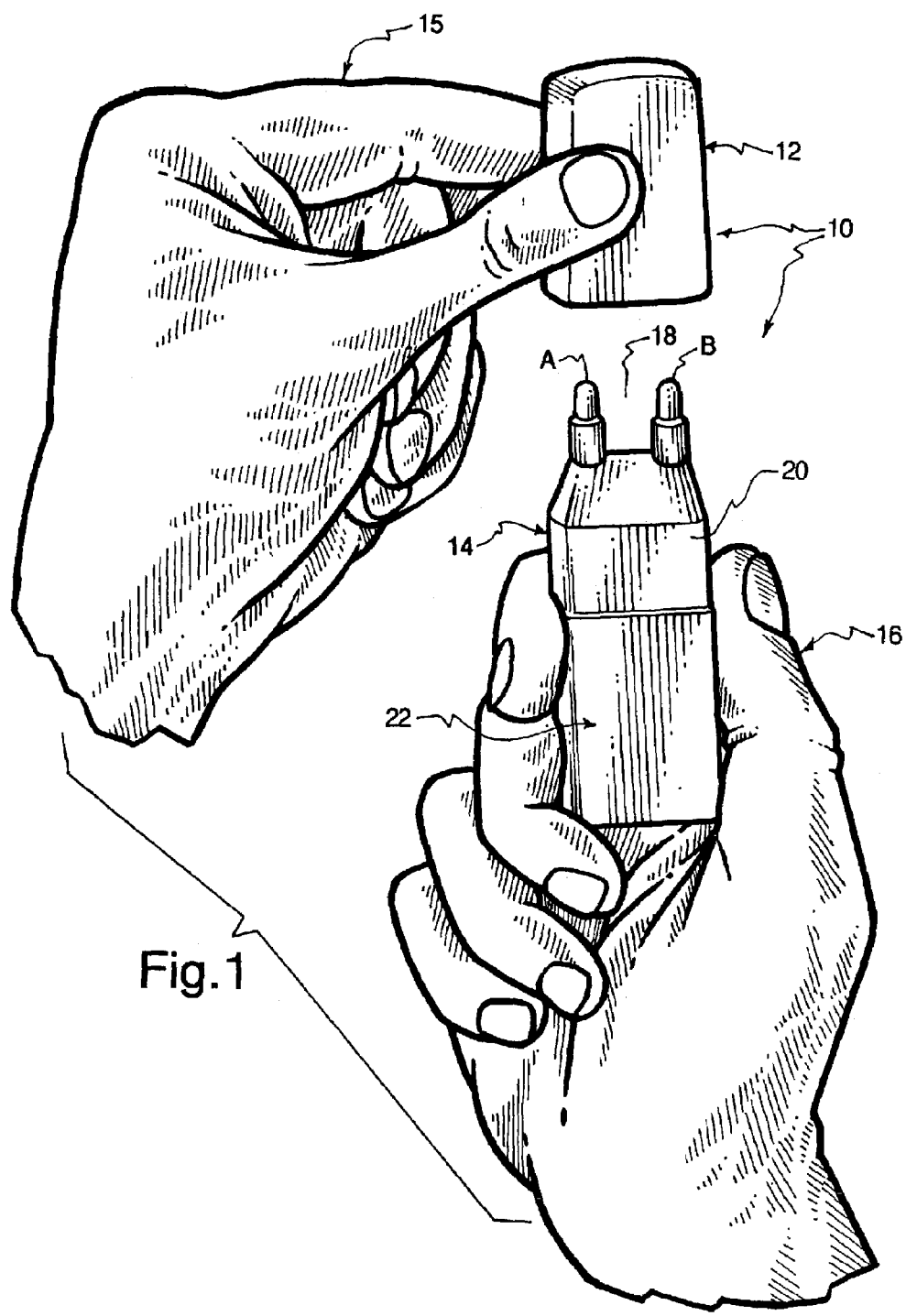
FIG. 1 is a perspective of a viral inhibitor embodying principles of the present invention.

The present invention addresses the long-standing, unsatisfied need for a viral-inhibiting non-invasive apparatus and methods. The novel apparatus and methods herein disclosed fundamentally impose an electric current signal of reversing polarity upon a viral-laden region, on a non-invasive basis. The apparatus is handy since it may be compact, such that some embodiments may be hand-held and self utilized, whereby the electric current signal passes between exposed spaced electrodes or probes through a viral-laden region of the person afflicted, such as a lip affected with a cold sore or fever blister. The polarity of the current signal, after a relatively short period of time, is rapidly reversed and oppositely applied also for a limited period of time. In some embodiments, the current signal, from a low-voltage power source, is applied to one electrode for a few seconds, the transition to reverse polarity takes only micro seconds and the oppositely applied current signal to a second electrode then also consumes a few seconds. However, the process may be repeated periodically without risk of human injury. The length of exposure may be shortened or extended, as appropriate. The reversal of polarity is accommodated by a trigger circuit interposed between two differential circuits.

The apparatus and associated methodology reduces the severity, frequency and duration of the viral phenomenon. The apparatus is cost effective, low maintenance and, while it may be functional for an extremely long time, it may be discarded and replaced when and if the device or probes thereof become contaminated so that complete cleaning can no longer take place. The disclosed apparatus is essentially painless, uses low power, has an automatic shutoff, conserves energy and may utilize one or more of a variety of waveforms. The apparatus includes a safety feature, which prevents harm to the user or to a child who may inadvertently gain access to the apparatus.

The reversal in polarity is significant, although the exact reason therefore is not, at this time, fully understood. There are no known side effects, merely a slight tingle at the skin.

The disclosed apparatus (inhibitor) includes a high current disabling circuit which shuts down the apparatus if the current signal passing between the electrodes through the viral-ridden tissue exceeds a safe range.

A double-pole, double-throw switch may be used to rapidly reverse polarity. The current signal, first in one direction and then in a second, comprises an output successively issued from two differential circuits through opposed probes or electrodes. The internal circuitry of the differential circuits in the disclosed apparatus comprises zero bias circuitry. The zero bias circuit is deactivated by manual engagement of a push button. The zero bias is restored when the reverse polarity signals time out, to preserve electrical power. High gain can be achieved and active discrete elements may be utilized in the inhibitor. A regeneration circuit can boot the inhibitor for rapid utilization.

The start push button is preferably interior of a transparent or translucent cover, which is yieldable to accommodate actuation of the start push button through the cover. Similarly, certain light indicators (LEDs) are disclosed as being inside the transparent or translucent casing. As explained herein in greater detail, the visual indicators communicate to the user that the device is activated, the direction of the current signal, that the magnitude of the current of the signal is either within or beyond a safe range. The inhibitor negates circuit bounce, which otherwise might cause multiple or false starts.

The two spaced electrodes or probes may be non-detachable and of a non-metallic conductive material to increase useful life, prevent corrosion and accommodate more effective cleaning between uses. The current signal between the electrodes preferably is disbursed or spread across a large region of the probe surface to reduce potential harm and to accommodate diffusion into all parts of the viral-laden area. A concentrated signal through metal probes might create a higher risk of injury to the user. The battery may be of any suitable type, although a commercially available nine (9) volt transistor radio battery of very small dimension is currently preferred. The useful life of such a battery in the disclosed apparatus can be for many years. Less voltage loss can occur with high gain and regeneration features if used to cause saturation of the output circuits. Soldered battery leads are preferred over snap connectors, for a longer reliable useful life because of less corrosion.

Reference is now made to the drawings wherein like numerals are used to designate like parts throughout. FIG. 1 illustrates a hand-held viral inhibitor, generally designated 10, embodying principles of the present invention. Inhibitor 10 comprises a removable, press-fit cap, generally designated 12, held in one had 15 of a user with the active portion of the device, generally designated 14, shown as being held in a second hand 16. The active portion 14 comprises a pair of spaced probes or electrodes "A" and "B" separated by a predetermined gap or space 18, where viral-laden tissue is placed. Adjacent to the electrodes A and B is a translucent casing 20, which is deflectable so as to accommodate actuation of a press start button located under the casing, as hereinafter explained in greater detail. The casing 20 also allows passage of illumination to the eyes of the user from certain visual indicators located under the translucent casing 20. The electrical components comprising the inhibitor 10 are disposed in casing 20. The active portion 14 of the inhibitor 10 further comprises a base housing 22 in which the 9 volt power supply battery 24 is located.

After each use, as explained herein, it is preferred that the probes or electrodes A and B be cleaned with alcohol or in some other similar way and the cap 12 once more positioned releasibly in press fit relation over the probes A and B and the translucent cover 20, for storage purposes.

The electronic components positioned in casing 20 are all initially zero biased so that during idle times, there is zero power drain. Therefore, the power supply 24 (FIG. 2), which may be a commercially available nine volt transistor radio battery is of high quality and has both a long shelf life and a long useful life.

Figure 2:
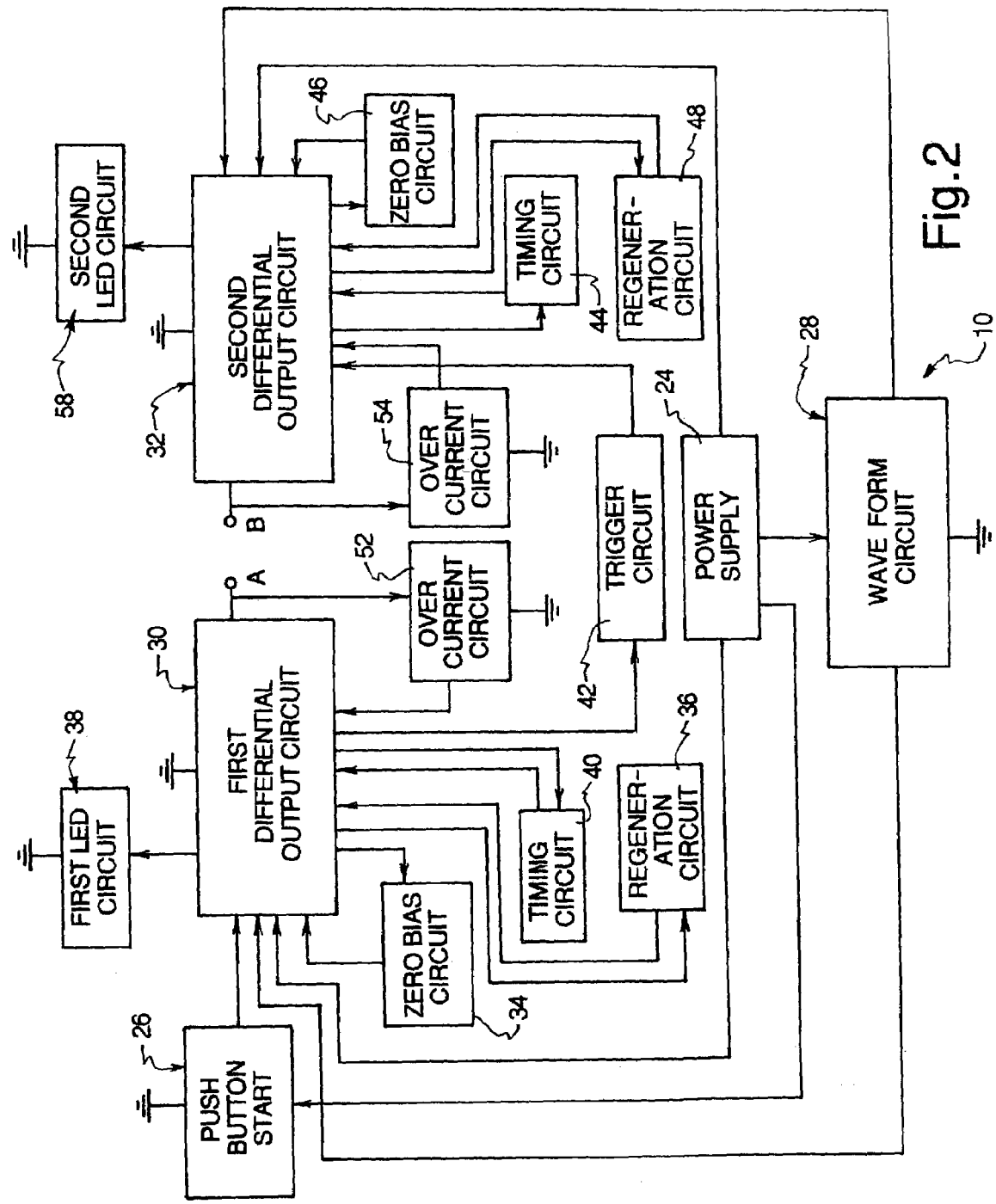
FIG. 2 is a block diagram of the electronics of the inhibitor of FIG. 1.

With continued reference to FIG. 2, the power supply 24 provides low voltage electrical power to push start button 26, to a waveform circuit 28 and to first and second differential output circuits 30 and 32.

Figure 3:
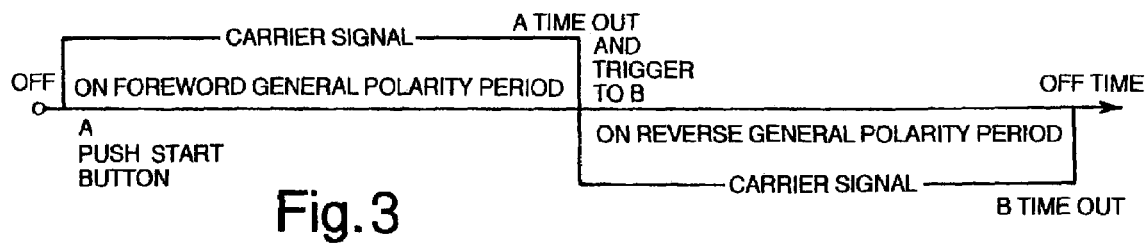
FIG. 3 is a diagram of the carrier signal upon which a desired waveform is superimposed.

The waveform circuit 28 may be of any commercially available type by which a desired signal is superimposed upon a carrier signal, and the composite signal issued first from first differential output circuit 30 and thereafter from second differential output circuit 32. The nature of the carrier signal is illustrated in FIG. 3. The signal from circuit 28, which is superimposed upon the carrier signal may be of any desired type, including, but not limited to, a sine wave, a half sine wave rectified, a full sine wave rectified, a positive or a negative ramp waveform, a square and other more sophisticated waveforms, a positive and a negative triangle waveform, a sawtooth waveform and a ramp wave form. Thus, the superimposed waveform may range from simplistic to complex, depending upon the type, in the best judgment of those skilled in the art, is deemed most appropriate for a given application. Thus, the output signal may be characterized as a carrier signal upon which a further waveform of appropriate makeup, is superimposed to provide the desired current signal saturation of a viral-laden location.

With both differential output circuits 30 and 32 in an off condition, a predetermined site on the translucent casing 20, is manually depressed by the user, which activates the first differential output circuit 30.

Once the start button 26 has activated differential output circuit 30 pressure on button 26 is released and the input to circuit 30 is fed back or regenerated to provide a high gain amplification output signal which is delivered to probe A. This signal propagates across space 18 to probe B. Space 18, during operation of the inhibitor 10, is occupied by a viral-laden region of tissue, such as a human lip comprised of a cold sore or fever blister. The high gain amplification in the first differential output circuit 30 drives the output at probe A to deep saturation with a near zero internal voltage drop causing the output signal voltage level to be near full battery voltage (typically nine volts).

When the first differential output circuit 30 is activated and delivers a low current signal to probe A, a first color LED or light indicator 38 is illuminated so as to be visually observable to the user through the translucent casing 20. This confirms that the first differential output circuit 30 is functioning appropriately and delivering a current signal to probe A, having a magnitude within a safe range.

Once the first differential output circuit 30 is on and a current signal being delivered to probe A, a timing circuit 40 controls the duration during which probe A receives the signal. When the timing circuit 40 times out, the first differential output circuit 30 is turned off and a trigger circuit 42 activates the second differential output circuit 32. This changes the state of second differential output circuit 32 from off to on, activating a timing circuit 44, which controls the length of time second differential output circuit 32 delivers a low current signal to probe B, which is passed through viral-laden tissue in space 18 back to probe A. Once the predetermined time set by timing circuit 44 has expired, the circuit 44 causes the second differential output circuit 32 to turn off. In this condition, no signal is issued to either probe A or B. The timing circuit 44 activates a regeneration which increases the gain, as explained above, in the signal issuing the second differential output circuit 32 to probe B.

When both differential output circuits 30 and 32 are off, the inhibitor 10 can be re-activated only by pushing start button 26 once more, which re-initiates the sequence described above.

As is true of the first differential output circuit 30, the second differential output circuit 32 provides a high gain amplification. When the second differential output circuit 32 is delivering a current signal to probe B, a second color LED or light indicator 50 is visually illuminated through the translucent casing 20 for visual observation by the user.

The probes A and B are monitored respectively by overcurrent circuits 52 and 54, respectively. Should the milliamp magnitude of the current signal between the probes exceed a predetermined amount, the overcurrent circuits 52 and 54 cause first and second differential and regeneration output circuits 30 and 32 to both be in an on condition so that no further current signal passes between probes A and B. Normally, current levels at the probes A and B will stay within the permitted range unless skin is wet. When wet both circuits 30 and 32 are placed in an on state, with both LED, 38 and 58 illuminated. The inhibitor 10 is then moved away from the viral-laden site, the skin dried and the process utilizing the inhibitor 10 is repeated. When both first and second differential output circuits are placed in an on condition, the first differential output circuit 30 turns off after the above-mentioned predetermined on time. Similarly, the second differential output circuit 32 turns off at the end of its normal reverse polarity predetermined interval.

Regeneration circuits 34 and 46 help feed back output signals from the first and second differential output circuits 30 and 32, respectively, to the inputs of circuits 30 and 32 to thereby obtain a high gain amplification, as explained in greater detail in conjunction with the circuit diagram of Figure A.

The timing circuits 40 and 44 comprise charging and discharging capacitors to set periods for each output sequence of first one polarity and then reverse polarity.

Each differential output circuit 30 and 32 is of such a nature that the circuits may be characterized as floating, where the output level and signal polarity flow direction is set by differences between the first and second differential output circuits 30 and 32. The circuitry of each circuit 30 and 32 is zero biased by circuits 34 and 46 during idle time to prevent drainage of power from the battery 24. Each circuit 30 and 32 comprises high gain active discrete elements or components so that the zero bias between the two circuits is balanced.

The probes A and B may be non-detachable and of a non-metallic conductive material having a desired low level of ohms resistance. Non-metallic conductive material better accommodates cleaning and spreads the signal across the entire tip area so as to permeate as much of the viral-laden tissues as possible. The spreading of the signal also eliminates any risk of burning, thereby making the inhibitor 10 safer.

As mentioned earlier, the casing 20 is preferably deflectable and translucent, or transparent to accommodate visual observation of the visual indicators 38 and 58 on the inside thereof and to accommodate, through deflection, actuation of push start button 26.

The present invention involves relatively few parts, commonly used components, easily obtained tolerances, is not temperature or humidity sensitive and provides a long, useful life. The circuitry may be mounted on one surface of a circuit board resulting in high reliability, and a lower cost. It is preferred that electrical connections be through direct coupling with soldered battery leads, as opposed to snap connectors for improved reliability because little or no corrosion occurs due to high moisture environments.

The resulting inhibitor is compact, inexpensive and replaceable, when and if it becomes contaminated after a protracted use. Viral inhibitors in accordance with the present invention and related methodology, solves a long standing previously unsatisfied problem pertaining to a non-invasive mechanism by which fever blisters, lesions, growths, warts, cold sores, herpes infections, shingles and other viruses are inhibited so that they become less severe, less frequent and of a shorter duration. The inhibitor may be hand-held and self utilized.

Figure 4:
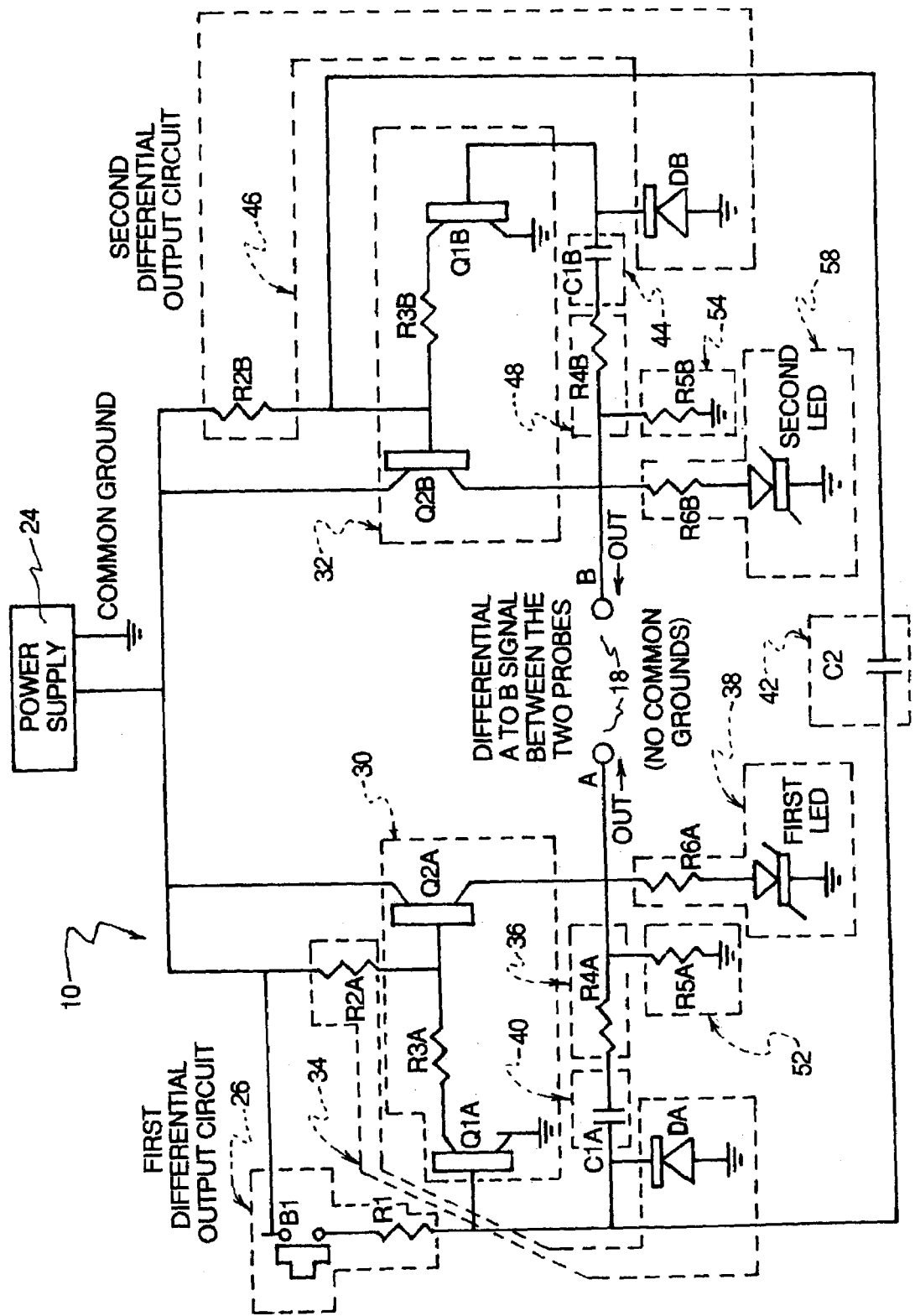
FIG. 4 is a circuit diagram of circuitry contained in the inhibitor of FIG. 1.

Reference is now made to FIG. 4 which illustrates the circuitry contained within the casing 20. The circuitry relates to components contained within blocks illustrated and described in conjunction with FIG. 2. When the inhibitor 10 is idle, zero bias circuits 34 and 46 provide a zero bias to the circuitry so that no battery drain occurs. Resistors $R2_A$ and $R2_B$ prevent energy loss to the circuits 30 and 32 when the inhibitor 10 is off. The combinations of resistor $R2_A$ and diode $D_A$ and resistor $R2_B$ and diode $D_B$, respectively, prevents leakage from inputs to transistors $Q1_A$, $Q2_A$, $Q1_B$ and $Q2_B$, hereinafter described, when inhibitor 10 is bled off by the zero bias circuits 34 and 46. By reason of resistors $R2_A$ and $R2_B$, leakages to ground through diodes $D_A$ and $D_B$ is prevented.

When the user or operator is ready to render the inhibitor 10 active, push start button 26 is manually depressed, which momentarily closes at B1, allowing current to flow across B1 through high ohm resistor R1 to the base of transistor $Q1_A$. Once resistor $Q1_A$ has been so triggered, the push start button 26 is manually released which places B1 in its normally open state. Once transistor $Q1_A$ is activated, the first differential circuit 30 is placed in operation so that, for a pre-determined interval of time, a current signal is communicated to probe A, through a viral-laden area to the probe B, as explained herein in greater detail.

The transistor $Q1_A$ of first differential output circuit 30 changes the signal delivered to the base by 180 degrees at the collector thereof. The emitter of transmitter $Q1_A$ is at ground. The signal at the collector is delivered across direct coupling resistor $R3_A$ to the base transistor $Q2_A$. The transistor $Q2_A$ changes the signal delivered to its base through 180 degrees at the collector thereof, to restore the signal to in-phase positive. The emitter of the transistor $Q2_A$ is at battery potential. The in-phase positive signal at the collector of the transistor $Q2_A$ is communicated to the probe A, to the LED circuit 38 and to a feedback and regeneration circuit 36 comprising resistor $R4_A$. This feedback signal is communicated across capacitor $C1_A$ to the base of transistor $Q1_A$ as high gain positive input to transistor $Q1_A$. This regenerates and elevates the signal to a higher level and causes the circuit 30 to rapidly change from low to high gain output and helps to drive transistor $Q2_A$ deeper into saturation to enhance the current signal at the probe A.

Once the first differential output circuit 30 is timed out by capacitor $C1_A$ of circuit 40, as explained herein in greater detail, the second differential circuit 32 is activated including turning transistors $Q1_B$ and $Q2_B$ on. The charge from capacitor C2 is delivered to the base of transistor $Q2_B$ turning transistor $Q2_B$ on. The emitter of transistor $Q2_B$ is at battery potential and the collector communicates a signal to second LED circuit 58, to regeneration circuit 48 and to probe B. The regeneration circuit 44 comprised of resistor $R4_B$ above achieves the same feedback high gain and amplification result for the second differential output circuit 32 to thereby ultimately deliver an enhanced high gain current signal to probe B.

This feedback regeneration, providing high gain amplification at the circuits 30 and 32 reduces the off-to-on time and reverse polarity transition time requirements. The circuits 30 and 32 are complimentary and symmetrical.

The on time of the first differential output circuit 30 is set by the timing capacitor $C1_A$, which is calibrated to retain circuit 30 in its on condition for the needed time interval. Once capacitor $C1_A$ is fully charged, which consumes time needed for circuit 30 to be on, insufficient voltage remains at the base of the transistor $Q1_A$ to keep transistor $Q1_A$ in an on state. Accordingly, transistor $Q1_A$ times out.

The high gain amplification and regeneration feedback feature of the invention allow smaller capacitors to provide the magnitude of on time needed.

Once the first differential output circuit 30 is timed out by capacitor $C1_A$, the second differential output circuit 32 is activated by the trigger circuit 42. As stated above, electric power stored in fully charged capacitor C2 is communicated to the base of the transistor $Q2_B$, turning it on. The emitter of the transistor $Q2_B$ is at battery potential, while the collector communicates to probe B, the second LED circuit 58 and feedback regeneration circuit 48 and timing circuit 44. The feedback signal flow through resistor $R4_B$ of regenerator circuit 48 to the base of transistor $Q1_B$ turning transistor $Q1_B$ on. Once transistor $Q1_B$ is turned on, feedback from the collector transistor $Q2_B$ through a feedback resistor $R4_B$ charges capacitor $C1_B$ for the predetermined interval of time required to reach a full charge, which equals the on time needed for circuit 32. Once capacitor $C1_B$ is fully charged, insufficient voltage reaches the base of the transistor $Q1_B$ to keep transistor $Q1_B$ on. Thus, circuit 32 then times out and the entire inhibitor 10 is placed in an off or inactive state. The regeneration of circuit 48 creates a high gain amplified signal to probe B.

The inhibitor 10 may be used successively, one time after another. The circuitry illustrated in FIG. 4 provides for fast restart recovery time from the end of the prior use to the beginning of the next use. This is accommodated by diodes $D_A$ and $D_B$, which provide paths for the timing capacitors $C1_A$ and $C1_B$ to discharge rapidly each time the associated differential output and regeneration circuit is turned off. As stated above, diodes $D_A$ and $D_B$ also aid the zero bias circuits 34 and 46 by keeping leakage to zero.

When the first differential output circuit 30 is on, the signal issuing from the collector of transistor $Q2_A$ is communicated not only through feedback timing circuit 40 and to probe A but also across resistor $R6_A$ to first LED 38, causing this LED to illuminate through the transparent or translucent casing 20. This visually informs the user that the current signal is at a safe milliamp level and is being transferred from electrode A to electrode B. Similarly, when the circuit 30 and LED 38 are off and the circuit 32 on, the high gain signal from the collector of transistor $Q2_B$ is not only displaced through circuit 44 and to probe B, but is delivered to the second LED 58 across resistor $R6_B$, to cause the second LED to be illuminated. This visually informs the user that the current signal is at a safe milliamp level and is being passed from electrode B to electrode A across space 18 occupied by viral-laden tissue of the user.

There may be occasions when the current level of the signal passing from one electrode to the other becomes higher than the recommended safety range, such as when a lip is placed in space 18, the surface of which has excessive moisture. By way of background, when the circuit 30 is on, providing a high output level signal to probe A, the circuit 32 is off, providing zero output to probe B. Thus, the current signal flows from probe A through viral-laden tissue to probe B and also through the high current level sensor resistor $R5_A$ of overcurrent circuit 52 to ground. When and if the current rises to an unacceptable level, such causes the voltage drop across resistor $R5_B$ to increase. The second differential output circuit 32 is turned on, while the first differential output circuit 30 remains on. In this state, both the first and second LEDs 38 and 58 are illuminated, visually disclosing the problem to the user. In this condition, the differential between the probes A and B is essentially zero and no signal current flows between the probes thereby discontinuing current signal flow through the viral-laden tissue and eliminating the risk of injury to the user independent of whether the user observes that both LEDs 38 and 58 are on.

Significantly, the connection between transistors $Q1_A$ and $Q2_A$ as well as between transistors $Q1_B$ and $Q2_B$, is a direct current coupling through resistors $R3_A$, and $R3_B$ respectively. This reduces the need for additional components, including capacitors and resistors. As a consequence, a number of problems are eliminated or alleviated including loss of power, dilution of signals, lower amplification gain and premature reduction in the regeneration feedback signal.

While the on time for each circuit 30 and 32 and the time required for reversal of polarity may vary, it is presently believed that circuit 30 should be on for 10 seconds or more and circuit 32 for 10 seconds or more with no more than 20 microseconds expiring during polarity reversal. The signal voltage across the probes A and B, in certain applications, should be less than 10 volts and current levels less than 1 milliamp.

It is presently preferred that transistors $Q1_A$ and $Q1_B$ each comprise a NPN semiconductor and transistors $Q2_A$ and $Q2_B$ each comprise a PNP complimentary semiconductor with symmetrical specifications.

The rapid reversal of polarity after circuit 30 is turned off and circuit 32 turned on is almost instantaneous. Capacitor $C1_A$ is saturated at the time, insufficient voltage is delivered to the base of transistor $Q1_A$, causing the circuit 30 to shut down, as explained above, at which time the capacitor C2 triggers to turn circuit 32 on. As stated above, this polarity reversal transition is in the microseconds range.

The signal from the collectors of transistor $Q1_A$ and $Q1_B$ across resistor $R3_A$ and resistor $R3_B$ to the base transistor $Q2_A$ and the base of transistor $Q2_B$ provides the highest possible amplification gain to drive transistor $Q2_A$ and transistor $Q2_B$ deep into saturation. This drops the minimum voltage across the associated emitter lead to the associated collector lead. Thus, most of the voltage source at the emitter lead comes out the collector lead to the output of the associated probe A or B.

While an independent waveform circuit, such as circuit 28 of FIG. 2, may be used to provide the optimum waveform to the probes A and B, the desired waveform may be generated internally within the circuit of FIG. 4, through not only the arrangement of the components but by careful selection of electronic elements to comprise the circuit.

The invention may be embodied in other specific forms without departing from the spirit or essential characteristics thereof. The present-embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A method of transcutaneously inhibiting viral phenomenon at a person's skin comprising the acts of:

superimposing an anti-viral signal upon a reversible carrier signal to produce a composite wave having a current less than one milliampere;

externally applying the less than one milliampere composite wave in one direction to flow across a viral-laden region of the skin between spaced electrodes for a first controlled interval of time whereby the composite wave disrupts viral activity in one flow direction;

essentially instantaneously reversing the carrier signal component of the composite wave to oppositely flow and externally apply the less than one milliampere composite wave across the viral-laden region between the spaced electrodes for a second controlled interval of time whereby the composite wave disrupts viral activity in a second flow direction.

2. A method according to claim 1 wherein first and second differential output circuits consecutively supply the composite current wave between the electrodes first in one direction and thereafter in the opposite direction.

3. A method according to claim 2 further comprising the act of timing out the method of claim 2 causing a rapid recovery of the differential output circuits and repeating the method of claim 2.

4. A method according to claim 1 wherein the composite wave passing between the electrodes tracks through a viral infested region.

5. A method according to claim 1 wherein the composite wave between electrodes comprises signals selected from the group consisting of sine wave, half wave rectified, full wave rectified and ramp.

6. A method according to claim 1 wherein the composite wave between electrodes comprise signals selected from the group consisting of square wave, triangular wave saw tooth and reverse ramp.

7. A method according to claim 1 wherein flow is reversed by a trigger circuit.

8. A method according to claim 1 wherein the method comprises use of a portable, hand-held device.

9. A method according to claim 1 wherein essentially instantaneously reversing act occurs in micro seconds and the output composite wave of less than one milliampere in each direction occupies a few seconds.

10. A method according to claim 1 wherein the current is derived from a low voltage source of electrical energy.

11. A method according to claim 1 comprising the further act of indicating to the user when the method is correctly operating within safe limits.

* * * * *